United States Patent [19]

Berger et al.

[11] 4,291,032
[45] Sep. 22, 1981

[54] THIAZOLO[3,2-c]BENZOXAZINE DERIVATIVES

[75] Inventors: Christian Berger, Le Plessis Robinson; Daniel Farge, Thiais; Claude Moutonnier, Le Plessis Robinson; Gerard Wolff, Thiais, all of France

[73] Assignee: Rhone Poulenc Industries, Paris, France

[21] Appl. No.: 192,988

[22] Filed: Oct. 2, 1980

[30] Foreign Application Priority Data

Oct. 5, 1979 [FR] France .............................. 79 24833

[51] Int. Cl.³ .................... A61K 43/90; C07D 513/04
[52] U.S. Cl. .................................. 424/248.51; 544/95
[58] Field of Search ...................... 424/248.51; 544/95

[56] References Cited

PUBLICATIONS

Kiprianov et al., Chemical Abstracts, vol. 69 (1968) 37081c.

*Primary Examiner*—Richard Raymond
*Attorney, Agent, or Firm*—Stevens, Davis, Miller & Mosher

[57] ABSTRACT

New thiazolo[3,2-c]-1,3-benzoxazine derivatives of the general formula (I), in which X is oxygen or sulfur, $R_1$ and $R_2$, which are identical or different, are hydrogen or halogen atoms or alkyl, alkoxy, alkylthio or trifluoromethyl radicals, in the 7-, 8-, 9- or 10-position, and $R_3$ is a hydrogen atom or a carboxyl radical, their salts, if appropriate, their preparation and the medicaments in which they are present.

These new derivatives are particularly useful as analgesic agents.

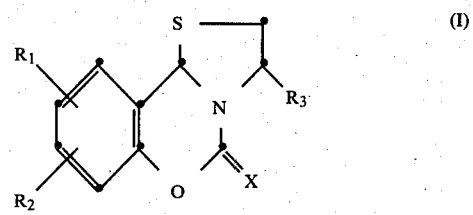

6 Claims, No Drawings

THIAZOLO[3,2c]BENZOXAZINE DERIVATIVES

The present invention relates to new thiazole-[3,2-c]-1,3-benzoxazine derivatives of the general formula:

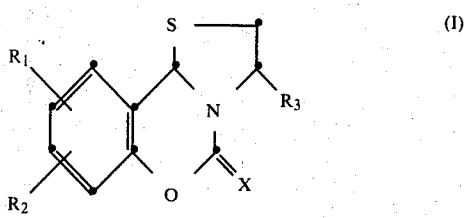

their salts, if appropriate, their preparation and the medicaments in which they are present.

In the general formula (I), the symbol X represents an oxygen or sulfur atom, the symbols $R_1$ and $R_2$ (which are identical or different) each represent a hydrogen or halogen atom or an alkyl, alkoxy, alkylthio or trifluoromethyl radical, in the 7-, 8-, 9- or 10-position, and the symbol $R_3$ represents a hydrogen atom or a carboxyl radical.

It is understood that the alkyl portions or radicals are linear or branched and contain 1 to 4 carbon atoms, and that the products in which $R_3$ is other than a hydrogen atom are derived from the L, D and D, L forms of cysteine.

According to the invention, the products of the general formula (I) can be obtained by reacting a product of the general formula:

(in which X is defined as above and the symbols Y, which are identical, represent chlorine atoms or imidazolyl, benzimidazolyl, triazolyl, benzotriazolyl or pyrazolyl radicals) with a thiazolidine derivative [if appropriate in equilibrium with its "imine" form, according to J. J. PESEK and J. H. FROST, Tetrahedron, 31, 907 (1975)] corresponding to the general formula:

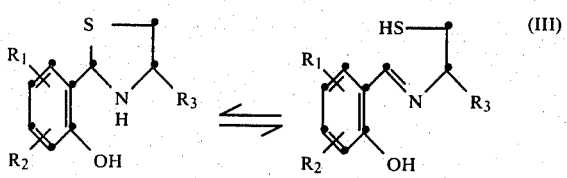

in which $R_1$, $R_2$ and $R_3$ are defined as above.

The reaction is generally carried out in an aromatic organic solvent (e.g. benzene or toluene), in a chlorinated solvent (e.g. methylene chloride, chloroform or 1,2-dichloroethane) or in an ether (e.g. ethyl ether, tetrahydrofuran or dioxane), at a temperature between −20° C. and the reflux temperature of the reaction mixture, and in the presence of a base, such as a nitrogen-containing organic base (e.g. triethylamine), when using a reagent of the general formula (II) in which Y represents a chlorine atom.

The products of the general formula (II) in which Y is other than a chlorine atom can be prepared in accordance with the method described by C. LARSEN, K. STELIOU and D. N. HARPP, J. Org. Chem. 43, 2, 337 (1978).

The thiazolidine derivatives of the general formula (III) can be obtained, by applying the method described by M. FATOME et al., Chim. Ther., 5, 312 (1970), or the method described in The Chemistry of Penicillins, page 962, Princeton University Press (1949), Princeton, N.J. (U.S.A.), from salicylaldehyde or one of its derivatives and from cysteamine or L-, D- or D,L-cysteine.

It is not absolutely necessary to isolate the thiazolidine derivative of the general formula (III) in order to carry out the reaction with the products of the general formula (II).

The substituted derivatives of salicylaldehyde can be prepared by applying the method described by G. CASIRAGHI et al., J.C.S. PERKIN I, 318 (1978).

If desired, the compounds of the present invention can be purified by physical methods, such as crystallization or chromatography.

If appropriate, the new products according to the invention can be converted to metal salts or to addition salts with a nitrogen-containing base, in the case where $R_3$ represents a carboxyl radical. These salts can be obtained by reaction with a metal base (in particular an alkali metal base or alkaline earth metal base), ammonia or a nitrogen-containing organic base, in a suitable solvent, such as an alcohol, an ether or water, or by an exchange reaction with a salt of an organic acid. The salt formed precipitates, if necessary after concentration of its solution; it is separated off by filtration or decantation.

The new products according to the invention and their salts possess remarkable pharmacological properties. They are particularly valuable analgesic agents. Some of them have also shown themselves to be anti-inflammatory and antipyretic agents.

The analgesic activity manifests itself in rats at doses of between 5 and 200 mg/kg, administered orally, using the technique of E. SIEGMUND et al., Proc. Soc. Exp. Biol. Med., 95, 729 (1957).

The anti-inflammatory activity manifests itself in rats at doses of between 25 and 250 mg/kg, administered orally, according to the technique of K. F. BENITZ and L. M. HALL [Arch. Int. Pharmacodyn., 144, 185 (1963)].

The antipyretic activity manifests itself in rats at doses of between 5 and 50 mg/kg, administered orally, using the technique of J. J. LOUX et al., Toxicol. Appl. Pharmacol., 22, 674 (1972).

Furthermore, the actue toxicity of the products according to the invention, expressed at their $LD_{50}$, is more than 900 mg/kg, administered orally to mice.

Of particular value are the products in the formula of which X represents an oxygen or sulfur atom, $R_1$ represents a hydrogen atom or an alkyl or alkoxy radical (as defined above), in the 7- or 9-position, $R_2$ represents a hydrogen atom and $R_3$ represents a hydrogen atom or a carboxyl radical.

Amongst these compounds, those in which $R_1$ and $R_2$ represent hydrogen atoms are preferred.

For medicinal purposes, the new compounds are used either in the form of the acid or in the form of pharmaceutically acceptable salts, that is to say salts which are non-toxic at the use doses, in the case where $R_3$ represents a carboxyl radical.

The following examples, which are given without implying a limitation, show how the invention can be put into practice.

EXAMPLE 1

85.4 g of 2-(2-hydroxyphenyl)-thiazolidine are dissolved in 300 cm³ of tetrahydrofuran. A solution of 93.3 g of N,N'-thiocarbonyldiimidazole in 700 cm³ of tetrahydrofuran is added in the course of 10 minutes. The mixture is heated to reflux for 20 minutes. The solution is then cooled to 20° C. and concentrated to dryness under reduced pressure (20 mm of mercury; 2.67 kPa) at 30° C. The residue is dissolved in 1,200 cm³ of methylene chloride. The resulting solution is washed with twice 1,500 cm³ of distilled water and dried over sodium sulfate. The solution is filtered in the presence of decolorizing charcoal and concentrated to dryness under reduced pressure (100 mm of mercury; 13.3 kPa) at 20° C. The residue is recrystallized from 1,000 cm³ of absolute ethanol. The crystals are filtered off and dried under reduced pressure (0.5 mm of mercury; 0.07 kPa) at 40° C. This yields 51.6 g of 5-thioxo-2,3,5,10b-tetrahydrothiazolo[3,2-c]-1,3-benzoxazine in the form of white crystals of instantaneous m.p. (Kofler)=127° C.

EXAMPLE 2

36.2 g of 2-(2-hydroxyphenyl)-thiazolidine are dissolved in 400 cm³ of methylene chloride. 35.6 g of N,N'-thiocarbonyldiimidazole are added and the reaction is allowed to proceed for 14 hours, whilst stirring. The solution is filtered and the filtrate is concentrated to dryness under reduced pressure (100 mm of mercury; 13.3 kPa) at 20° C. The residue is dissolved in 350 cm³ of ethyl acetate. The resulting solution is washed with twice 300 cm³ of water and then dried over sodium sulfate and filtered in the presence of decolorizing charcoal. The filtrate is concentrated to dryness under reduced pressure (20 mm of mercury; 2.67 kPa) at 40° C. The residue is taken up in 60 cm³ of ethanol. The crystals are filtered off and dried under reduced pressure (0.5 mm of mercury; 0.07 kPa) at 40° C. This yields 9.9 g of 5-thioxo-2,3,5,10b-tetrahydrothiazolo[3,2-c]-1,3-benzoxazine, the characteristics of which are identical to those of the product of Example 1.

EXAMPLE 3

A solution of 10 g of 2-(2-hydroxyphenyl)-thiazolidine and 15.4 cm³ of triethylamine in 50 cm³ of tetrahydrofuran is added dropwise, so as to maintain a temperature of 30° C., to a solution of 4.2 cm³ of thiophosgene in 50 cm³ of tetrahydrofuran. The mixture is stirred for a further 30 minutes at 20° C. after the addition has ended. The solvent is evaporated off to dryness under reduced pressure (20 mm of mercury; 2.67 kPa) at 40° C. and the residue is redissolved in a mixture of 100 cm³ of ethyl acetate and 100 cm³ of water. The aqueous phase is separated off by decantation and the organic phase is washed with 100 cm³ of a saturated aqueous solution of sodium bicarbonate and then with 100 cm³ of distilled water. The organic phase is dried over sodium sulfate and filtered in the presence of decolorizing charcoal. The solvent is evaporated off to dryness under reduced pressure (20 mm of mercury; 2.67 kPa) at 40° C. This yields 7.3 g of 5-thioxo-2,3,5,10b-tetrahydrothiazolo[3,2-c]-1,3-benzoxazine, the characteristics of which are identical to those of the product of Example 1.

EXAMPLE 4

14 cm³ of triethylamine are added to a suspension of 11.6 g of cysteamine hydrochloride in 80 cm³ of 1,2-dichloroethane. The mixture is heated under reflux and 10.5 cm³ of salicylaldehyde are then added in the course of 2 minutes. The mixture is heated under reflux for 15 minutes and the water formed is entrained by azeotropic distillation. A solution of 22.2 g of N,N'-thiocarbonyldiimidazole in 80 cm³ of 1,2-dichloroethane is then added in the course of 2 minutes. The mixture is subsequently kept under reflux for 10 minutes and then cooled to 20° C. The resulting solution is washed with three times 150 cm³ of distilled water. The organic phase is dried over sodium sulfate, filtered in the presence of decolorizing charcoal and then concentrated under reduced pressure (20 mm of mercury; 2.67 kPa), at 40° C., to a volume of 20 cm³. This solution is filtered on a column (diameter 3 cm) containing 60 g of silica. Elution is carried out with 200 cm³ of 1,2-dichloroethane. The filtrate and the eluate are concentrated to dryness under reduced pressure (20 mm of mercury; 2.67 kPa) at 40° C. and the residue is dissolved in 15 cm³ of ethyl acetate under reflux. The solution is cooled and kept at 4° C. for 1 hour. The crystals are filtered off. This yields 2.2 g of 5-thioxo-2,3,5,10b-tetrahydrothiazolo[3,2-c]-1,3-benzoxazine, the characteristics of which are identical to those of the product of Example 1.

EXAMPLE 5

22.7 g of N,N'-thiocarbonyldiimidazole are added to a solution of 25 g of 2-(5-chloro-2-hydroxyphenyl)-thiazolidine in 270 cm³ of tetrahydrofuran. The resulting solution is heated under reflux for 25 minutes. The solution is then cooled and kept at 0° C. for 1 hour. The resulting crystals are filtered off, washed with twice 30 cm³ of cold tetrahydrofuran and dried under reduced pressure (0.5 mm of mercury; 0.07 kPa) at 40° C. This yields 11 g of 9-chloro-5-thioxo-2,3,5,10b-tetrahydrothiazolo[3,2-c]-1,3-benzoxazine in the form of white crystals.

Instantaneous m.p. (Kofler)=261° C.

EXAMPLE 6

23.1 g of N,N'-thiocarbonyldiimidazole are added to a solution of 25 g of 2-(2-hydroxy-3-methoxyphenyl)-thiazolidine in 270 cm³ of tetrahydrofuran. The resulting solution is heated under reflux for 25 minutes. The solution is cooled and kept at 0° C. for 2 hours. The crystals formed are filtered off and then washed with twice 50 cm³ of cold tetrahydrofuran and dried under reduced pressure (0.5 mm of mercury; 0.07 kPa) at 40° C. This yields 12.5 g of white crystals of 7-methoxy-5-thioxo-2,3,5,10b-tetrahydrothiazolo[3,2-c]-1,3-benzoxazine.

Instantaneous m.p. (Kofler)=173° C.

EXAMPLE 7

25.3 g of N,N'-thiocarbonyldiimidazole are added to a solution of 30 g of 2-(2-hydroxy-5-methoxyphenyl)-thiazolidine in 300 cm³ of tetrahydrofuran. The mixture is stirred, heated under reflux for 10 minutes and then cooled to 20° C. The solvent is evaporated off under reduced pressure (20 mm of mercury; 2.67 kPa) at 40° C. and the residue is dissolved in 300 cm³ of ethyl acetate. The solution is washed with 3 times 200 cm³ of distilled water, the organic phase is then dried over sodium sulfate and the solution is filtered. The solvent is evaporated off under reduced pressure (20 mm of mercury; 2.67 kPa) at 40° C. and the resulting residue is chromatographed on a column (diameter 6 cm) containing 500 g of silica. Elution is carried out with 4,000 cm³ of an ethyl acetate/cyclohexane mixture (3/7 by volume), 500 cm³ fractions being collected. Fractions 4 to 7 are combined and the solvent is evaporated off to dryness under reduced pressure (20 mm of mercury; 2.67 kPa) at 40° C. The resulting product is taken up in 100 cm³ of ether and the insoluble white crystals are filtered off. This yields 7.5 g of 9-methoxy-5-thioxo-2,3,5,10b-tetrahydrothiazolo[3,2-c]-1,3-benzoxazine.

Instantaneous m.p. (Kofler)=134° C.

EXAMPLE 8

45.25 g of 2-(2-hydroxyphenyl)-thiazolidine are dissolved in 500 cm³ of methylene chloride. 40.5 g of N,N'-carbonyldiimidazole are added and the reaction is allowed to proceed for 14 hours, whilst stirring. The solution is concentrated to dryness under reduced pressure (100 mm of mercury; 13.3 kPa) at 20° C. The residue is taken up in 500 cm³ of ethyl acetate and the resulting solution is washed with twice 500 cm³ of distilled water. The organic phase is dried over sodium sulfate, filtered in the presence of decolorizing charcoal and then concentrated to dryness under reduced pressure (20 mm of mercury; 2.67 kPa) at 40° C. The resulting oily residue is chromatographed on a column (diameter 60 mm) containing 500 g of silica. Elution is carried out successively with mixtures of ethyl acetate and cyclohexane of increasing ethyl acetate concentration (10/90 by volume: 4,000 cm³, then 20/80 by volume: 4,000 cm³). 350 cm³ fractions are collected. Fractions 11 to 13 are combined and concentrated to dryness under reduced pressure (0.5 mm of mercury; 0.07 kPa) at 40° C. This yields 12 g of white crystals of 5-oxo-2,3,5,10b-tetrahydrothiazolo[3,2-c]-1,3-benzoxazine.

Instantaneous m.p. (Kofler)=77° C.

EXAMPLE 9

28 cm³ of triethylamine are added to a suspension of 45 g of L-4-carboxy-2-(2-hydroxyphenyl)-thiazolidine in 600 cm³ of methylene chloride and the mixture is then stirred for 20 minutes at 20° C. 71.2 g of N,N'-thiocarbonyldiimidazole are added and the mixture is stirred at 20° C. for 18 hours. The solvent is then evaporated off under reduced pressure (100 mm of mercury; 13.3 kPa) at 20° C. and the residue is taken up in 500 cm³ of distilled water. The aqueous phase is covered with 500 cm³ of ethyl acetate and the mixture is stirred. The pH of the mixture is brought to 2 by adding 4 N hydrochloric acid. The organic phase is decanted and the aqueous phase is extracted with 3 times 100 cm³ of ethyl acetate. The organic phases are combined and extracted with 500 cm³ of a saturated aqueous solution of sodium bicarbonate. The aqueous phase is covered with 100 cm³ of ethyl acetate and acidified to pH=2 by adding 4 N hydrochloric acid. The organic phase is separated off by decantation, dried over sodium sulfate, then filtered in the presence of decolorizing charcoal and finally concentrated to dryness under reduced pressure (20 mm of mercury; 2.67 kPa) at 40° C. The resulting oily residue is dissolved in 600 cm³ of an ethanol/water mixture (1/1 by volume). The solution is kept at 4° C. for 1 hour and the crystals are then filtered off and dried. This yields 9.2 g of 3-carboxy-5-thioxo-2,3,5,10b-tetrahydrothiazolo[3,2-c]-1,3-benzoxazine in the form of white crystals.

Instantaneous m.p. (Kofler)=225° C. (decomposition).

203 mg of 3-carboxy-5-thioxo-2,3,5,10b-tetrahydrothiazolo[3,2-c]-1,3-benzoxazine are dissolved in a solution of 64 mg of sodium bicarbonate in 7.6 cm³ of water. The resulting solution is evaporated to dryness under reduced pressure (20 mm of mercury; 2.67 kPa) at 40° C. and the residue is taken up in 25 cm³ of diethyl ether. The suspension is filtered and the solid is dried under reduced pressure (0.5 mm of mercury; 0.07 kPa) at 20° C. This yields 190 mg of the sodium salt of 3-carboxy-5-thioxo-2,3,5,10b-tetrahydrothiazolo[3,2-c]-1,3-benzoxazine in the form of a white powder.

Infrared spectrum (KBr): characteristic bands (cm$^{-1}$): 1,615, 1,460 and 750.

EXAMPLE 10

24 cm³ of triethylamine are added to a suspension of 38.4 g of L-4-carboxy-2-(2-hydroxyphenyl)-thiazolidine in 200 cm³ of tetrahydrofuran. The mixture is heated under reflux until dissolution is complete and a solution of 60.7 g of N,N'-thiocarbonyldiimidazole in 300 cm³ of tetrahydrofuran is then added in the course of 5 minutes. The mixture is kept under reflux for 10 minutes and then cooled and concentrated to dryness under reduced pressure (20 mm of mercury; 2.67 kPa) at 40° C. The resulting residue is taken up in 200 cm³ of a saturated aqueous solution of sodium bicarbonate. The mixture is washed with twice 200 cm³ of ethyl acetate and the aqueous phase is then covered with 200 cm³ of ethyl acetate and acidified to pH=2 by adding 4 N hydrochloric acid. The organic phase is separated off by decantation. The aqueous phase is re-extracted with 100 cm³ of ethyl acetate. The organic phases are combined, dried over sodium sulfate, filtered in the presence of decolorizing charcoal and concentrated to dryness under reduced pressure (20 mm of mercury; 2.67 kPa) at 40° C. This yields 7.5 g of 3-carboxy-5-thioxo-2,3,5,10b-tetrahydrothiazolo[3,2-c]-1,3-benzoxazine.

EXAMPLE 11

35 g of 2-(2-hydroxy-5-methylphenyl)-thiazolidine are dissolved in 350 cm³ of methylene chloride. 35.1 g of N,N'-thiocarbonyldiimidazole are added and the mixture is heated under reflux for 1 hour. The resulting solution is washed with 500 cm³ of distilled water and then dried over magnesium sulfate and filtered in the presence of decolorizing charcoal. The filtrate is concentrated to dryness under reduced pressure (20 mm of mercury; 2.67 kPa) at 40° C. The residue is taken up in 100 cm³ of ethyl acetate. The crystals are filtered off and dried under reduced pressure (0.5 mm of mercury; 0.07 kPa) at 40° C. This yields 8.9 g of 9-methyl-5-thioxo-2,3,5,10b-tetrahydrothiazolo[3,2-c]-1,3-benzoxazine in the form of white crystals of instantaneous m.p. (Kofler): 159° C.

EXAMPLE 12

By following the procedure described in Example 11, using 15 g of 2-(5-fluoro-2-hydroxyphenyl)-thiazolidine and 14.7 g of N,N'-thiocarbonyldiimidazole in 150 cm³ of methylene chloride, 7.5 g of 9-fluoro-5-thioxo-2,3,5,10b-tetrahydrothiazolo[3,2-c]-1,3-benzoxazine are obtained in the form of white crystals of instantaneous m.p. (Kofler): 180° C.

The medicaments consisting of a derivative of the general formula (I) in the pure state, if appropriate in the form of the free acid or a pharmaceutically acceptable salt, and the pharmaceutical compositions in which the derivative is present in association with at least one compatible and pharmaceutically acceptable diluent or adjuvant, constitute a further subject of the present invention. These compositions can be administered orally, rectally, parenterally or topically.

Tablets, pills, powders, coated tablets or granules can be used as solid compositions for oral administration. In these compositions, the active product according to the invention is mixed with one or more inert diluents, such as sucrose, lactose or starch. These compositions can also comprise substances other than diluents, e.g. a lubricant, such as magnesium stearate.

Solutions, suspensions, syrups, elixirs containing inert diluents, such as paraffin oil, and pharmaceutically acceptable emulsions can be used as liquid compositions for oral administration. These compositions can also comprise substances other than diluents, e.g. wetting, sweetening or flavoring products.

The compositions, according to the invention, for parenteral administration can be suspensions, emulsions or aqueous or non-aqueous sterile solutions. Water, propylene glycol, polyethylene glycol, vegetable oils, in particular olive oil, and injectable organic esters, e.g. ethyl oleate, can be employed as the solvent or vehicle. These compositions can also contain adjuvants, in particular wetting agents, emulsifiers or dispersing agents. Sterilization can be carried out in several ways, e.g. using a bacteriological filter, by incorporating sterilizing agents into the composition, by irradiation or by heating. The compositions can be prepared in the form of sterile solid compositions which can be dissolved in an injectable sterile medium at the time of use.

The compositions for rectal administration are suppositories which can contain excipients, such as cacao butter or suppository wax, in addition to the active product.

The compositions for topical application are presented, in particular, in the form of ointments.

The medicaments according to the invention are particularly useful in human therapy for their analgesic and, if appropriate, anti-inflammatory and antipyretic action. They are particularly indicated for the treatment of acute and chronic pains, rheumatic and traumatic algias, dental, neurological and visceral pains, various algias (pains experienced by cancer patients), inflammatory diseases (ankylosing spondylarthritis, acute articular rheumatism and arthrosis) and, if appropriate, febrile states.

In human therapy, the doses depend on the desired effect and the duration of the treatment; for an adult, they are generally between 100 and 2,000 mg per day.

In general, the physician will decide the posology which he considers to be most appropriate as a function of the age, the weight and all the other factors peculiar to the subject to be treated.

The following examples, which are given without implying a limitation, illustrate a composition according to the invention.

EXAMPLE A

Tablets containing 100 mg doses of active product and having the following composition are prepared in accordance with the usual technique:

| | |
|---|---|
| 5-thioxo-2,3,5,10b-tetrahydrothiazolo[3,2-c]-1,3-benzoxazine | 0.100 g |
| starch | 0.110 g |
| precipitated silica | 0.035 g |
| magnesium stearate | 0.005 g |

EXAMPLE B

A solution containing 110 mg/cm$^3$ of the sodium salt of 3-carboxy-5-thioxo-2,3,5,10b-tetrahydrothiazolo[3,2-c]-1,3-benzoxazine is prepared in water for injectable preparations. The resulting solution is divided up under aseptic conditions into ampoules at a rate of 5 cm$^3$ per ampoule. The ampoules are sealed and each contain 0.5 g of 3-carboxy-5-thioxo-2,3,5,10b-tetrahydrothiazolo[3,2-c]-1,3-benzoxazine (in the form of its sodium salt).

We claim:

1. A thiazolo[3,2-c]-1,3-benzoxazine derivative of the formula:

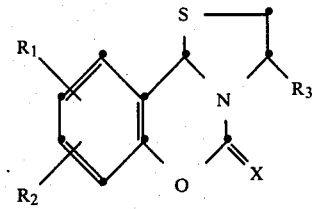

in which X represents an oxygen or sulfur atom, the symbols $R_1$ and $R_2$, which are identical or different, each represent a hydrogen or halogen atom or an alkyl, alkoxy, alkylthio or trifluoromethyl radical, in the 7-, 8-, 9- or 10-position, and $R_3$ represents a hydrogen atom or a carboxyl radical, the alkyl radicals and portions being linear or branched and containing 1 to 4 carbon atoms, and also its metal salts and its addition salts with nitrogen-containing organic bases, in the case where $R_3$ represents a carboxyl radical, in its diastereoisomeric forms and mixtures thereof.

2. A compound according to claim 1, in which $R_1$ represents a hydrogen or halogen atom or an alkyl or alkoxy radical, in the 7- or 9-position, $R_2$ represents a hydrogen atom and $R_3$ and X are defined according to claim 1.

3. A compound according to claim 1, in which $R_1$ and $R_2$ represent hydrogen atoms and $R_3$ and X are defined according to claim 1.

4. A compound according to claim 1, which is 5-thioxo-2,3,5,10b-tetrahydrothiazolo[3,2-c]-1,3-benzoxazine.

5. A compound according to claim 1, which is 3-carboxy-5-thioxo-2,3,5,10b-tetrahydrothiazolo[3,2-c]-1,3-benzoxazine.

6. A pharmaceutical composition which contains a thiazolo[3,2-c]-1,3-benzoxazine derivative as claimed in claim 1 or, if appropriate, a pharmaceutically acceptable salt of this product, in association with at least one pharmaceutically acceptable diluent.

* * * * *